United States Patent [19]

Shimura et al.

[11] Patent Number: 5,014,045
[45] Date of Patent: May 7, 1991

[54] RADIATION IMAGE READ-OUT APPARATUS USING MENU

[75] Inventors: Kazuo Shimura; Yuuma Adachi, both of Kanagawa, Japan

[73] Assignee: Fuji Photo Film Co., Ltd., Kanagawa, Japan

[21] Appl. No.: 330,833

[22] Filed: Mar. 30, 1989

[30] Foreign Application Priority Data

Mar. 31, 1988 [JP] Japan ................................. 63-80069

[51] Int. Cl.⁵ .......................... G09F 3/02; G09F 15/00; G01T 1/11; H04N 5/32
[52] U.S. Cl. ................................... 340/712; 250/337; 364/413.22; 358/111
[58] Field of Search ............................. 340/712, 721; 364/413.22, 300; 250/337, 327.1, 327.2, 484.1, 459.1; 358/111

[56] References Cited

U.S. PATENT DOCUMENTS

| | | | |
|---|---|---|---|
| 4,641,242 | 2/1987 | Kimura | 250/337 |
| 4,779,080 | 10/1988 | Coughin et al. | 340/721 |
| 4,821,211 | 4/1989 | Torres | 364/300 |

FOREIGN PATENT DOCUMENTS

| | | |
|---|---|---|
| 0181518 | 5/1986 | European Pat. Off. . |
| 55-12429 | 1/1980 | Japan . |
| 55-116340 | 9/1980 | Japan . |
| 55-163472 | 12/1980 | Japan . |
| 56-11395 | 2/1981 | Japan . |
| 56-104645 | 8/1981 | Japan . |
| 61-5193 | 2/1986 | Japan . |

Primary Examiner—Alvin E. Oberley
Assistant Examiner—Chanh Nguyen
Attorney, Agent, or Firm—Sughrue, Mion, Zinn, Macpeak & Seas

[57] ABSTRACT

A radiation image read-out apparatus comprises a read-out component, an image processing component, and a menu item display and selection component. The menu item display and selection component are constituted of a storage section for storing menu items and corresponding read-out conditions, an object portion designation section for designating the portion of the object whose image is to be read out, an image recording method designation section for designating the image recording method by which the image was recorded, a mode selection section for selecting one menu from among a plurality of menus constituted by classifying a large number of menu items which have once been classified with respect to all possible combinations of object portion and image recording condition, a display section for displaying the menu items, a selection section for selecting a displayed menu item, and a processing section for reading from the storage section menu items relating to the designated object portion and image recording method and forwarding the read-out menu items to the display section, reading menu items from the storage section and forwarding them to the display, and forwarding to the read-out component the read-out condition correponding to the required item.

4 Claims, 4 Drawing Sheets

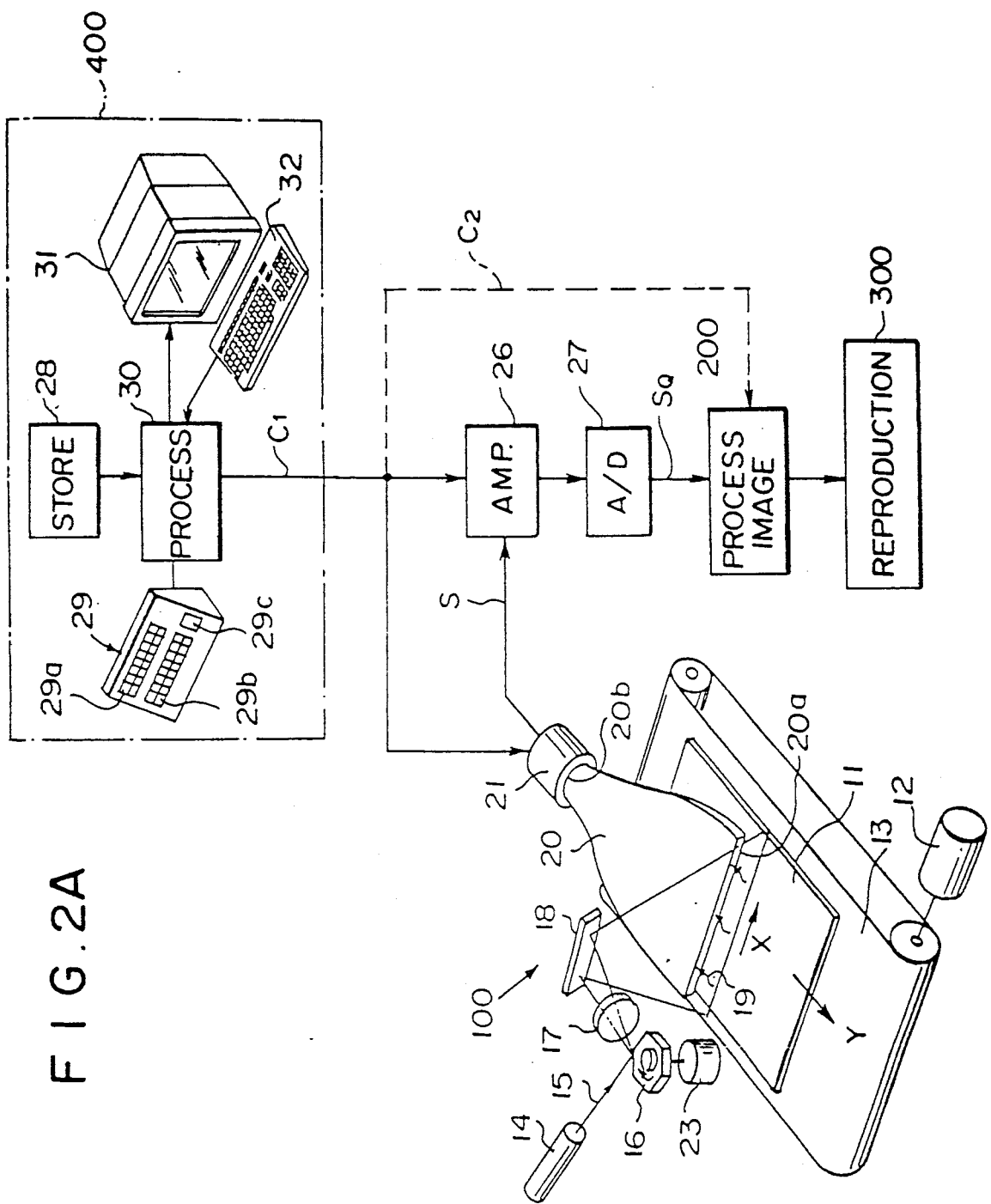

RADIATION IMAGE READ-OUT APPARATUS USING MENU

BACKGROUND OF THE INVENTION

1. Field of the Invention

This invention relates to a radiation image read-out apparatus which scans an image recording sheet such as a stimulable phosphor sheet on which radiation image information relating to an object is recorded to thereby obtain an image signal representing the radiation image and carries out image processing of the image signal.

2. Description of the Prior Art

Techniques for reading out a recorded radiation image to obtain an image signal, carrying out appropriate image processing of the image signal, and then reproducing and recording a visible image by use of the processed image signal have heretofore been known in various fields. For example, as disclosed in Japanese Patent Publication No. 61(1986)-5193, an X-ray image is recorded on an X-ray film having a small gamma value designed for the type of image processing to be carried out, the X-ray image is read out from the X-ray film and converted into an electric signal, and the electric signal (image signal) is image-processed and then used when the X-ray image is reproduced as a visible image on a copy photograph or the like. In this manner, a visible image having good image quality and exhibiting such characteristics as high contrast, high sharpness, excellent graininess property and the like can be reproduced.

Also, when certain kinds of phosphors are exposed to radiation such as X-rays, α-rays, β-rays, γ-rays, cathode rays or ultraviolet rays, they store part of the energy of the radiation. Then, when the phosphor which has been exposed to the radiation is exposed to stimulating rays such as visible light, light is emitted by the phosphor in proportion to the amount of energy stored during exposure to the radiation. A phosphor exhibiting such properties is referred to as a stimulable phosphor. As disclosed in Japanese Unexamined Patent Publication Nos. 55(1980)-12429, 56(1981)-11395, 55(1980)-163472, 56(1981)-104645 and 55(1980)-116340, it has been proposed to use stimulable phosphors in radiation image recording and reproducing systems. Specifically, a sheet provided with a layer of the stimulable phosphor (hereinafter referred to as a stimulable phosphor sheet) is first exposed to radiation which has passed through an object such as the human body in order to store a radiation image of the object thereon, and is then scanned with stimulating rays, such as a laser beam, which cause it to emit light in proportion to the amount of energy stored during exposure to the radiation. The light emitted by the stimulable phosphor sheet upon stimulation thereof is photoelectrically detected and converted into an electric image signal, which is used when the radiation image of the object is reproduced as a visible image on a recording material such a photographic film, a display device such as a cathode ray tube (CRT), or the like.

The radiation image recording and reproducing system using a stimulable phosphor sheet is advantageous over conventional radiography using a silver halide photographic material in that the image can be recorded over a very wide range (latitude) of radiation exposure. More specifically, since the amount of light emitted upon stimulation after the radiation energy is stored on the stimulable phosphor varies over a very wide range in proportion to the amount of energy stored thereon, it is possible to obtain an image which is unaffected by variations in the amount of exposure of the stimulable phosphor to the radiation, even when the amount of exposure varies greatly depending on the imaging conditions, by reading out the emitted light with a photoelectric conversion means at an appropriate read-out gain and converting it to an electric image signal to reproduce a visible image on a recording medium such as photographic film or on a display device such as a CRT.

The read-out condition used at the time of obtaining an image signal and/or the image processing condition used at the time of carrying out image processing with respect to the image signal are specified as items of a menu compiled by statistically analyzing and classifying a large number of radiation images. The classification is based on, for example, what portion of an object is represented by the recorded image (e.g. the head, the neck, the chest or the like in the case where the object is a human body) and what recording mode was used when the image was recorded (e.g. ordinary image recording mode, contrasted image mode, tomographic image mode or the like). Further subclassification, resulting in further menu items, is carried out for specific combinations of the portion of the object and the imaging condition. For example, ordinary image recording of the chest is subclassified into ordinary image recording of the thoracic vertebrae (frontal), the ribs, the clavicle, the scapula and the like.

The need for providing a menu including separate items for the respective read-out conditions and/or image processing conditions will be explained with respect to a specific example.

One condition that should be considered in setting the read-out condition and/or image processing condition is that regarding the treatment of unnecessary portions recorded on the image recording sheet at the time of image recording. Such unnecessary portions occur, for example, at parts of the image recording sheet which are exposed only to scattered radiation or to radiation which directly impinges on the image recording sheet without being transmitted or reflected by the object or which are recorded with images of portions of the object which are not required to be observed. Generally, the read-out condition and/or image processing condition are set to distinguish between the image signals corresponding to the radiation image required to be reproduced and the image signals corresponding to the unnecessary portions.

FIG. 3 is a graph showing a histogram of the quantity L of light emitted during read-out of an image of the chest of a human being in a system employing a stimulable phosphor sheet.

In this figure, the light quantity L emitted by the stimulable phosphor sheet when it is scanned with stimulating light is plotted on the horizontal axis, which has a logarithmic scale, and the frequency of occurrence of emitted light quantity values are plotted on the upper portion of the vertical axis. The image signal $S_Q$ obtained by photoelectric conversion of the light emitted by the stimulable phosphor sheet is plotted on the lower portion of the vertical axis, which has a logarithmic scale.

As shown, the histogram can be divided into 5 regions A-E which correspond respectively to the mediastinum, the heart, the lungs, the skin and soft parts, and regions outside the object.

Where a visible output image encompassing the whole of the mediastinum (region A), the heart (region B) and the lungs (region C) is desired, the read-out condition is set so that the image information falling between $L_{min}$ and $L_1$ is appropriately reproduced. More specifically, the read-out condition is set such that $L_{min}$ and $L_1$ within the range of light quantities L will respectively give rise to the minimum image signal $Q_{min}$ and the maximum image signal $Q_{max}$ corresponding to the minimum density $D_{min}$ and the maximum density $D_{max}$ within the range of densities appropriate for the output visible image. What this means is that the read-out condition falls along the straight line $G_1$ shown in the figure.

On the other hand, if the aforesaid read-out condition (corresponding to the $G_1$) should be used in a case where it is desired to observe only the heart, the image information corresponding to the heart would be converted to an image signal $S_Q$ covering only the range between $Q_1$ and $Q_2$. As this is narrower than would be the case if the image information corresponding to the heart only should be converted to an image signal covering the maximum range between $Q_{min}$ and $Q_{max}$ (corresponding to the line $G_2$), the density resolution of the output visible image will be lower in proportion to the difference. Therefore, where it is desired to observe only the heart (region B), the final read-out condition is set to corresponding to the line $G_2$ so as to ensure read-out of the image information corresponding to the heart with maximum resolution.

For reasons that will be apparent from the example just explained, read-out conditions and/or image processing conditions are defined in correspondence to a large number of image-recording menu items. The problem thus arises as of how to ensure that the menu item required for a particular read-out and image processing operation can be input with good operational efficiency and freedom from input error.

SUMMARY OF THE INVENTION

The primary object of the present invention is to provide a radiation image read-out apparatus which improves the operational efficiency at the time of designating the required menu item from among a large number of menu items classified in accordance with the image recording condition at the time the image of the object was recorded and which reduces the likelihood of error in making such a designation.

FIGS. 1A and 1B are overall views of two different arrangements of the radiation image read-out apparatus according to the present invention.

With reference to Figure 1A, the first radiation image read-out apparatus in accordance with this invention comprises:

read-out means 1 for scanning with a light beam a stimulable phosphor sheet, a photographic film or other image recording sheet on which a radiation image of an object has been stored, detecting light representing the radiation image emitted from the image recording sheet, and converting the detected light into an image signal, image processing means 2 for receiving the image signal from the read-out means 1 and carrying out image processing of the image signal, and menu item display and selection means 3 for displaying at least some of a large number of menu items classified in accordance with image recording conditions used at the time the radiation image of the object was recorded such that each menu item corresponds to a specific read-out condition and/or image processing condition to be used at the time of obtaining the image signal, enabling selection of a single menu item from among the menu items, and forwarding to the read-out means 1 and/or the image processing means 2 read-out condition $C_1$ and/or image processing condition $C_2$ corresponding to the selected menu item, as one of the image read-out conditions.

The menu item display and selection means 3 is constituted of:

a storage section 3a for storing the large number of menu items and the large number of read-out conditions and/or image processing conditions corresponding to the menu items, an object portion designation section 3b for designating, as one of the image recording conditions, the portion of the object whose image was recorded, an image recording method designation section 3c for designating, as one of the image recording conditions, the image recording method by which the image was recorded, designation section 3d for designating one or more routine menu items selected and registered in advance from among the large number of menu items, a display section 3e for displaying menu items, a selection section 3f for selecting the required one of the menu items displayed on the display section 3e, and a processing section 3g for, at the time of receiving an object portion designation from the object portion designation section 3b and an image recording method designation from the image recording method designation section 3c, reading from the storage section 3a the menu items relating to the designated object portion and image recording method and forwarding the read-out menu items to the display section 3e, for, at the time of receiving a routine menu item designation, reading the routine menu item or items from the storage section 3a and forwarding the same to the display section 3e, and for, at the time of receiving a required menu item selection from the selection section 3f, forwarding to the read-out means 1 and/or the image processing means 2 the read-out condition $C_1$ and/or the image processing condition $C_2$ corresponding to the required menu item.

The "light representing the radiation image emitted from the image recording sheet" mentioned above includes light emitted by a stimulable phosphor sheet, light transmitted through a photographic film, light reflected by a photographic film, and the like.

The routine menu item(s) can be fixed at the one or ones initially set or, alternatively, the processing section 3g can be provided with a counter for counting the number of times each of the menu items has been selected via the selection section 3f and the routine menu items can be changed in accordance with the counts recorded by this counter.

FIG. 1B is a block diagram showing a second radiation image read-out apparatus in accordance with this invention which, similarly to the apparatus of FIG. 1A, comprises a read-out means 1, an image processing means 2 and a menu item display and selection means designated as 3'. The menu item display and selection means 3' is different from the menu item display and selection means 3 shown in FIG. 1A. Specifically, the menu item display and selection means 3' is constituted of:

a storage section 3a' for storing the large number of menu items and the large number of read-out conditions and/or image processing conditions corresponding to the menu items, an object portion designation section 3b' for designating, as one of the image recording conditions, the portion of the object whose image was recorded, an image recording method designation section 3c' for designating, as one of the image recording conditions, the image recording method by which the image was recorded, a mode selection section 3d' for selecting one menu from among a plurality of menus constituted by classifying a large number of menu items which have once been classified with respect to all possible combinations of object portion and image recording condition, a display section 3e' for displaying image menu items, a selection section 3f' for selecting the required one of the menu items displayed on the display section 3e', and a processing section 3g' for, at the time of receiving an object portion designation from the object portion designation section 3b' and an image recording method designation from the image recording method designation section 3c', reading from the storage section 3a' those menu items relating to the designated object portion and image recording method which belong to the menu 15 designated in advance in the mode selection section 3d' and forwarding the read-out menu items to the display section 3e', and for, at the time of receiving a required menu item selection from the selection section 3f', forwarding to the read-out means 1 and/or the image processing means 2 the read-out condition $C_1$ and/or the image processing condition $C_2$ corresponding to the required menu item.

Some of the "plurality of image recording menus each constituted of a large number of menu items" mentioned above may include one or more identical menu items.

The menu items belonging to the aforesaid menus can be fixed at the ones initially set or, alternatively, the processing section 3g' can be provided with a counter for counting the number of times each of the menu items has been selected via the selection section 3f' and the menu items belonging to at least one image recording menu can be changed in accordance with the count recorded by this counter.

The first radiation image read-out apparatus according to this invention shown in FIG. 1A has the menu item display and selection means 3 which is provided with the routine designation section 3d for designating menu items which have been selected for registration from among a large number of menu items. When one or more routine menu items has been designated by the routine designation section 3d, the designated routine menu item or items are read from the storage section 3a and forwarded to the display section 3e, where they are displayed. The required one of the displayed routine menu items is then selected via the selection section 3f. This arrangement makes it possible to select and register in advance those menu items which relate to frequently conducted image recording operations so that the required menu item is generally included among and can be selected from these routine menu items. As a result, the efficiency of the operation of selecting the required menu item can be enhanced and the likelihood of an erroneous selection being made can be reduced.

Once the routine menu items have been established, they can be left unchanged. If desired, however, it is also possible to provide the processing section 3g with a counter for counting how many times each of the menu items is designated via the selection section 3f and to appropriately change the routine menu items in accordance with the results of this count. Changing the routine menu items in this way provides a further improvement in operating efficiency since it ensures that the most frequently used menu items will be displayed.

The second radiation image read-out apparatus according to this invention shown in FIG. 1B is provided with the mode selection section 3d' for selecting one menu from among a plurality of menus constituted by classifying a large number of menu items which have once been classified with respect to all possible combinations of object portion and image recording condition. Thus designation of the object portion at the object portion designation section 3b' and designation of the image recording method at the image recording method designation section 3c' does not cause all of the menu items classified under the particular combination of object portion and image recording method to be displayed, but causes display of only those of the classified menu items which have been grouped together as being menu items related to modes of image recording occurring with high frequency. Limiting the number of menu items displayed on the display section 3e' in this way makes the display easier to read and facilitates the selection of the required menu item. Thus, as in the case of the first radiation image read-out apparatus according to this invention shown in FIG. 1A, the efficiency with which the required menu item can be selected is improved while the likelihood of making an error in the selection is reduced.

The menu items belonging to the aforesaid menus can be fixed at the ones initially set or, alternatively, as was mentioned earlier, the processing section 3g' can be provided with a counter for counting the number of times each of the menu items has been selected via the selection section 3f and the menu items belonging to one image recording menu appropriate as the ordinarily displayed menu can be changed in accordance with the count recorded by this counter. Changing the menu items in this way provides a further improvement in operating efficiency since it ensures that the most frequently used menu items will always be displayed.

BRIEF DESCRIPTION OF THE DRAWINGS

FIGS. 2A and 2B are perspective views of two different embodiments of the radiation image read-out apparatus according to the present invention.

DESCRIPTION OF THE PREFERRED EMBODIMENTS

Figure 1A:
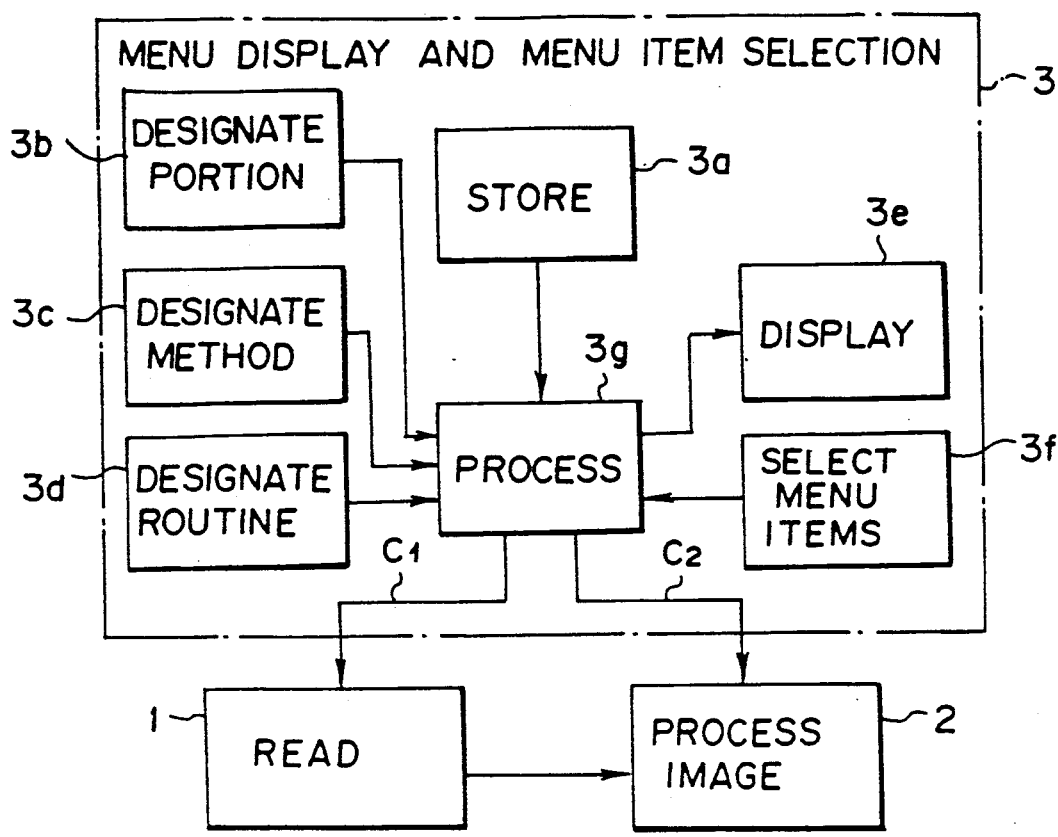
FIGS. 1A and 1B are block diagrams showing the overall arrangement of two different radiation image read-out apparatuses in accordance with the present invention.
Figure 1B:
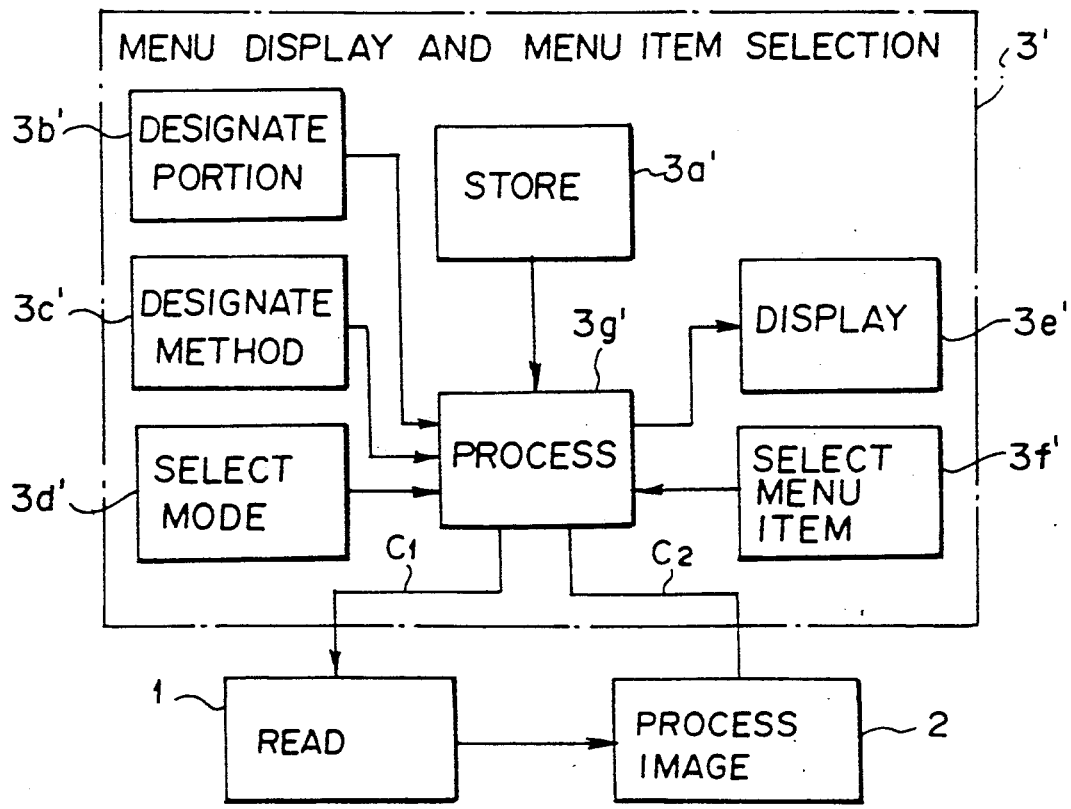

The invention will now be explained with reference to specific embodiments.

The embodiment of the radiation image read-out apparatus according to the present invention shown in FIG. 2A is a system employing a stimulable phosphor sheet.

A stimulable phosphor sheet 11 on which a radiation image has been stored is placed at a predetermined position in a read-out means 100. The so-positioned stimulable phosphor sheet 11 is conveyed in a sub-scanning direction indicated by the arrow Y by a sheet conveyance means 13 constituted of an endless belt or the like operated by a motor 12. On the other hand, stimulating rays 15 produced by a laser beam source 14 are reflected and deflected by a rotating polygon mirror 16, which is quickly rotated by a motor 23 in the direction indicated by the arrow, and the stimulating rays 15 pass through a converging lens 17 constituted of an fθ lens or the like. The direction of the optical path of the stimulating rays 15 is then changed by a mirror 18, and the stimulating rays 15 impinge upon the stimulable phosphor sheet 11 and scan across it in a main scanning direction indicated by the arrow X. The main scanning direction is approximately normal to the sub-scanning direction indicated by the arrow Y. When the stimulable phosphor sheet 11 is exposed to the stimulating rays 15, the exposed portion of the stimulable phosphor sheet 11 emits light 19 with an intensity proportional to the amount of energy stored during exposure to radiation. The emitted light 19 is guided by a light guide member 20, and photoelectrically detected by a photomultiplier 21 which acts as a photodetector. The light guide member 20 is made from a light guiding material such as an acrylic plate, and has a linear light input face 20a positioned so that it extends along the main scanning line on the stimulable phosphor sheet 11, and a ring-shaped light output face 20b is positioned in close contact with a light receiving face of the photomultiplier 21. The emitted light 19 entering the light guide member 20 through its light input face 20a is guided through repeated total reflection inside of the light guide member 20, emanates from the light output face 20b, and is received by the photomultiplier 21. In this manner, the intensity of the emitted light 19, which carries the information about the radiation image, is converted into an electric signal (analog output signal S) by the photomultiplier 21.

The analog output signal S generated by the photomultiplier 21 is amplified by an amplifier 26, and digitized by an A/D converter 27 into a read-out image signal $S_Q$.

The so-obtained read-out image signal $S_Q$ is sent to an image processing means 200 where it is subjected to appropriate image processing. The image processed signal is then forwarded to a reproducing apparatus 300, which uses it to reproduce a visible radiation image.

The read-out condition used in the read-out means 100 for obtaining the emitted light 19 and the image signal will now be explained.

In FIG. 2A, the reference numeral 400 denotes a menu item display and selection means, which includes a storage section 28, an operation panel 29, a processing section 30, a CRT display 31 and a keyboard 32.

A large number of menu items and a large number of read-out conditions established for the menu items are stored in the storage section 28.

The operation panel 29 has an object portion designation section 29a through which the object portion whose radiation image is to be read out is designated from among a large number of object portions (such as the head, the neck, the chest and the like). It also has an image recording method designation section 29b through which the recording method by which the radiation image to be read out was recorded is designated from among a large number of image recording methods (such as ordinary image recording, contrasted image recording, tomographic image recording and the like). When the object portion and the image recording method have been designated through these two sections 29a and 29b, they are forwarded to the processing section 30. The processing section 30 then reads from the storage section 28 the menu items which have been classified under the designated combination of object portion and image recording method (for example, in the case of ordinary image recording of the chest, the menu items read out would be general view of chest, thoracic vertebrae (frontal), ribs, clavicle, scapula and the like) and sends the read-out menu items to the CRT display 31, where they are displayed. The keyboard 32, which constitutes the selection section, is then used to select from among the menu items displayed on the CRT display 31 the one which is suitable for the radiation image to be read out in the read-out means 100. When the required menu item is input via the keyboard 32, the processing section 30 reads from the storage section 28 the read-out condition $C_1$ associated with the input menu item and forwards the same to the read-out means 100. In the read-out means 100, the read-out condition $C_1$ is used for setting the voltage applied to the photomultiplier 21 and the gain of the amplifier 26, whereby the read-out means 100 conducts read-out in accordance with the so-established read-out condition in the manner described earlier.

In the method of operation just described, it is necessary to use the operation panel 29 for designating a specific object portion from among a large number of such object portions and for designating a specific image recording method from among a large number of such methods. In an alternative method of operation, however, it suffices to press a button 29c, which constitutes the routine designation section. Pressing the button 29c causes specific frequently used menu items which have been selected and registered in advance from a cross-section spanning a large number of object portions and image recording methods to be read from the storage section 28 and displayed on the CRT display 31. It is thus possible to reduce the likelihood of errors in the designation of the object portion and the image recording method and, as a result, there is realized an improvement in the efficiency of selecting the required menu items.

Figure 2B:
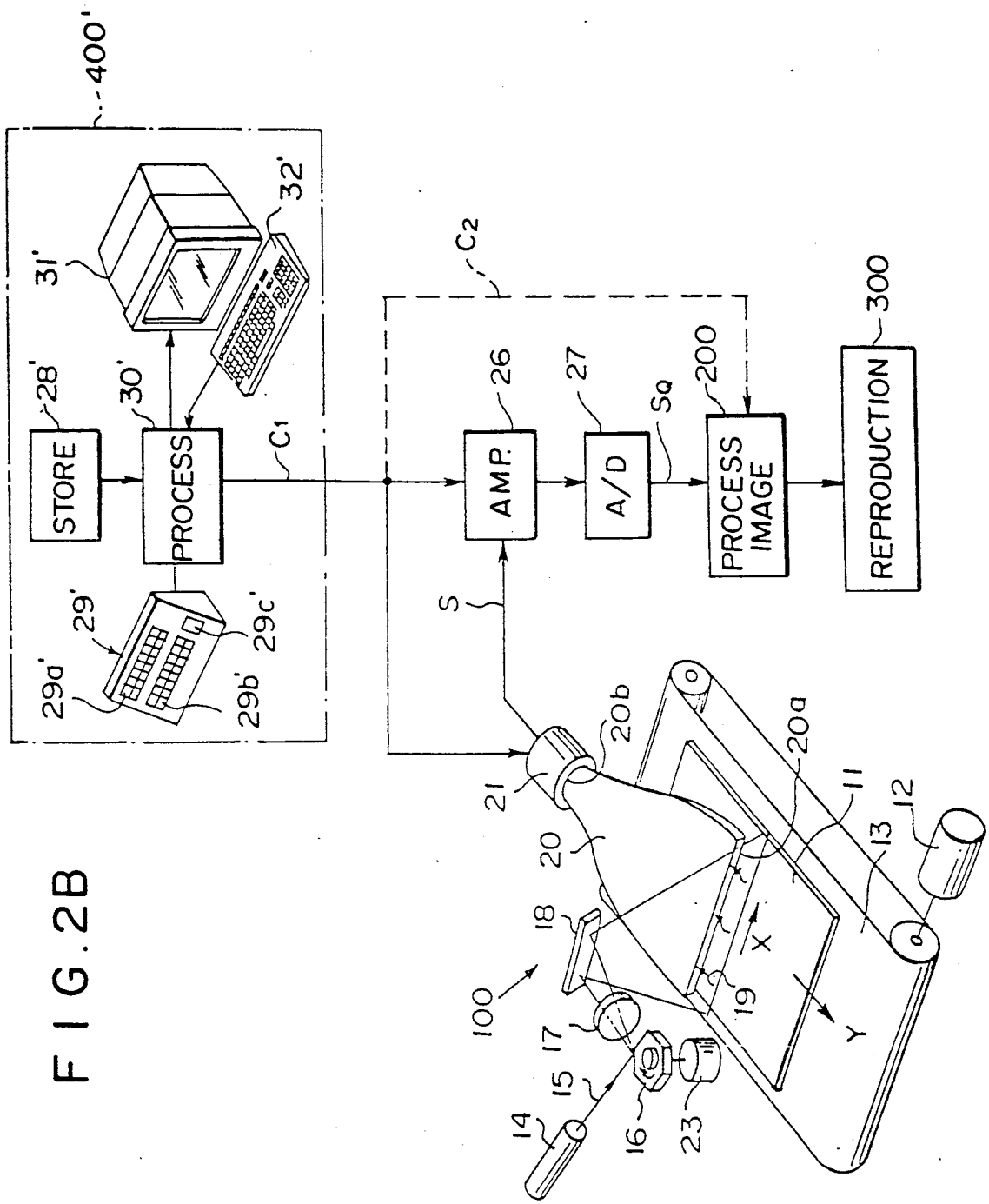
Figure 3:
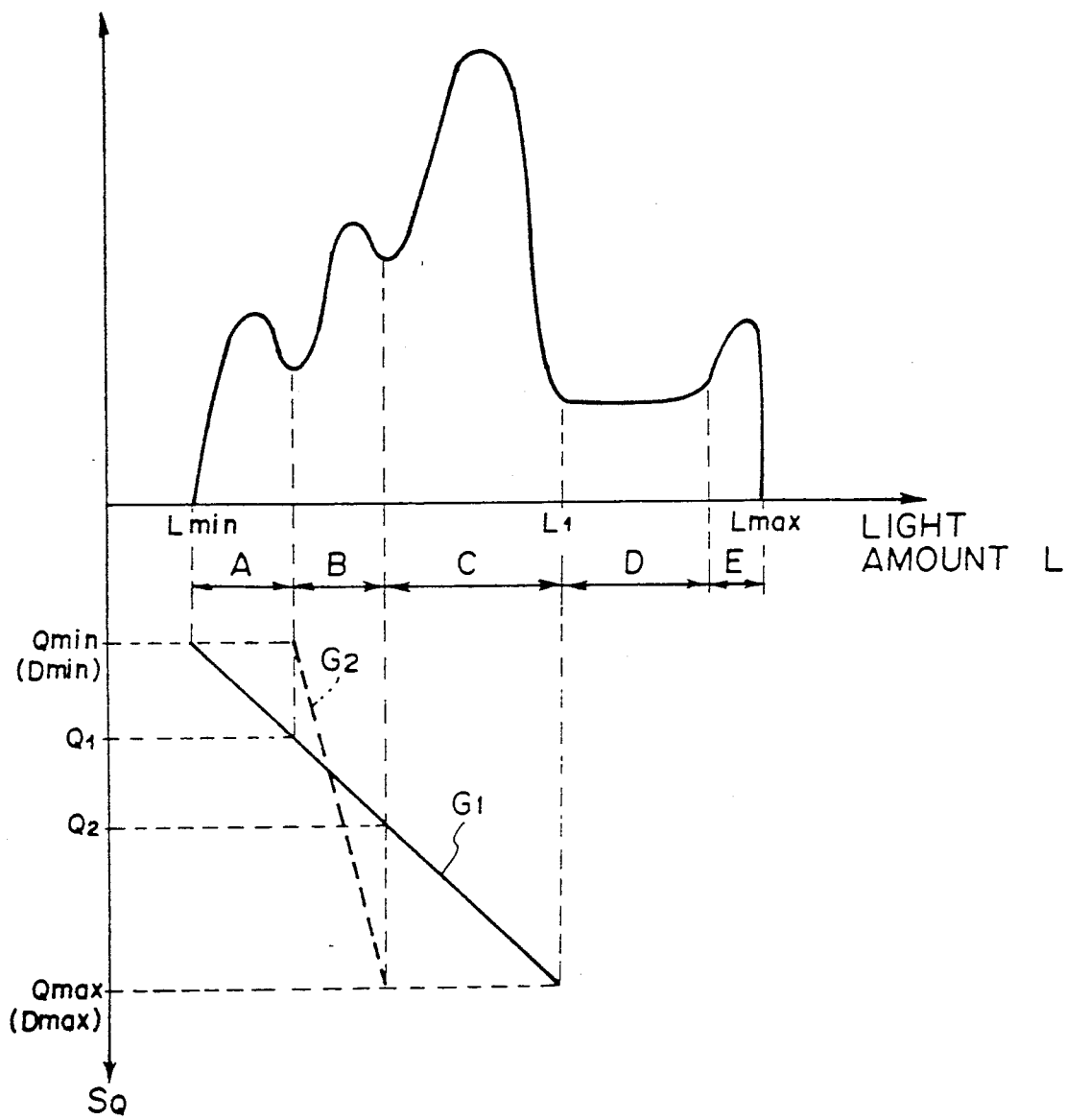
FIG. 3 is a histogram of the quantity of light emitted during read-out of the image of a human chest.

FIG. 2B is a perspective view of a second embodiment of the radiation image read-out apparatus according to the present invention, in which similar elements are numbered with the same reference numerals with respect to FIG. 2A.

The menu item display and selection means 400' of this embodiment has a storage section 28' in which is stored at least two menus constituted by classifying a large number of menu items which have once been classified with respect to all possible combinations of object portion and image recording condition. The classification of the menu items under the plurality of menus is such that menu items relating to frequently used image recording conditions are classified under a first menu and those relating to less frequently used image recording modes are classified under a second menu.

The object portion of whose image is to be read out is designated from among a large number of such object portions through an object portion designation section 29a' of an operation panel 29' and the image recording method is designated from among a large number of such methods through an image recording method designation section 29b'. The designations made in this way are input to a processing section 30' which, on the basis thereof, reads from the storage section 28' only those of the menu items classified under the designated combination of object portion and image recording method which are classified as belonging to the first menu, which is the menu normally selected through a mode selection section button 29c' and is comprised of frequently used menu items. The read-out items of the first menu are displayed on a CRT display 31'. For example, where ordinary image recording of the chest has been designated, the processing section 30' reads from among the menu items classified under this combination (general view of chest, ribs, clavicle, scapula, sternum, lungs, etc.) only those which have been classified under the first menu made up of menu items associated with frequency used radiation image recording modes (general view of chest, sternum and lungs). After the read-out menu items have been displayed on the CRT display 31', the required one is selected via a keyboard 32'. When the required menu item is input via the keyboard 32', the processing section 30' reads from the storage section 28' the read-out condition $C_1$ associated with the input menu item and forwards the same to the read-out means 100. Selection back and forth between the aforesaid first and second menus is possible simply by repeated pushing of the button 29c'. It is thus also possible when necessary to display and select the items of the second menu.

In the aforesaid embodiments, the menu item display and selection means 400 (400') outputs the read-out condition used at the time of reading out an image signal in the read-out means 100. Alternately, however, it is possible to have the storage section 28 (28') of the menu item display and selection means 400 (400') store image processing conditions corresponding to the respective menu items, for use during image processing in the image processing means 200, and to have the image processing condition $C_2$ corresponding to the menu item selected via the keyboard 32 (32') output to the image processing means 200 at the time the selection is made. With this arrangement, the read-out can be conducted independently of the menu items using a read-out condition which enables read-out of the emitted light over a wide range of light quantities extending from weak to intense and which is thus appropriate for the radiation image regardless of the condition under which it was recorded. Then when the so-obtained image signal $S_Q$ is image processed in the image processing means 200, it can be processed using the image processing condition $C_2$.

It is also possible to have the menu display and selection means 400 (400') output both the read-out condition $C_1$ and the image processing condition $C_2$.

Moreover this invention can be applied not only to apparatuses which employ stimulable phosphor sheets but can be applied widely to conventional apparatuses using X-ray film or generally to any other type of radiation image read-out apparatus which scans an image recording sheet on which a radiation image of an object has been recorded, obtains an image signal by reading out the light emitted by image recording sheet while it is being scanned, and carries out image processing on the image signal in accordance with an image processing condition.

As has been explained in detail in the foregoing, in accordance with one aspect of the present invention, there is provided a routine designation section which designates routine menu items which have been selected and registered in advance from among a large number of menu items and when the routine designation section designates one or more menu items that are associated with frequently used image recording modes, the designated routine menu items are read from a storage section and displayed on a display section. The required one of the displayed routine menu items can then be selected through a selection section so that the read-out condition and/or the image processing condition corresponding to the selected menu item will be sent to a read-out means and/or an image processing means. It is thus possible by a simple operation to display only the menu items which are associated with frequently used image recording modes. As a result, the operation of selecting the required menu item can be carried out with high efficiency and with minimal likelihood of an erroneous designation being made.

It is further possible in accordance with this aspect of the invention to provide the processing section with a counter for counting the number of times each of the menu items has been selected via the selection section, and to appropriately change the routine menu items in accordance with the number of times they have been used. This even further enhances the operational efficiency since it ensures that the most commonly used menu items will always be displayed regardless of any fluctuations that may occur in the frequency of use among the menu items.

In a second aspect of the invention, instead of providing the routine designation section, menus are constituted by classifying menu items which have already once been classified with respect to all possible combinations of object portion and image recording condition, and a mode selection section is provided for selecting the one of these menus which includes the menu items which are most frequently used. As a result, the number of menu items that are displayed is reduced, making the menu items easier to read and also reducing the amount of skill required in selecting the required menu item through the selection section. As a result, the efficiency of the menu item selection operation is improved and the likelihood of making an erroneous designation is reduced.

It is further possible in accordance with this aspect of the invention to provide the processing section with a counter for counting the number of times each of the menu items has been selected via the selection section, and to appropriately change the menu items included in the ordinarily displayed menu in accordance with the number of times they have been used. This even further enhances the operational efficiency since it ensures that the most commonly used menu items will always be displayed regardless of any fluctuations that may occur in the frequency of use among the menu items.

We claim:

1. A radiation image read-out apparatus comprising:
   (i) read-out means for scanning with a light beam an image recording sheet on which a radiation image of an object has been stored, detecting light representing said radiation image emitted from said image recording sheet, and converting said detected light into an image signal,
   (ii) image processing means for receiving said image signal from said read-out means and carrying out image processing of said image signal, and
   (iii) menu item display and selection means for displaying at least some of a large number of menu items classified in accordance with image recording conditions used at the time said radiation image of the object was recorded such that each menu item corresponds to a specific read-out condition and/or image processing condition to be used at the time of obtaining said image signal, enabling selection of a single menu item from among said menu items, and forwarding to said read-out means and/or said image processing means a read-out condition and/or image processing condition corresponding to said selected menu item, as one of said image read-out conditions wherein said menu item display and selection means is constituted of:

(a) a storage section for storing said large number of menu items and said large number of read-out conditions and/or image processing conditions corresponding to said menu items, (b) an object portion designation section for designating, as one of said image recording conditions, said portion of the object whose image was recorded, (c) an image recording method designation section for designating, as one of said image recording conditions, said image recording method by which said image was recorded, (d) a routine designation section for designating one or more routine menu items selected and registered in advance from among said large number of menu items, (e) a display section for displaying menu items, (f) a selection section for selecting a required one of the menu items displayed on said display section, and (g) a processing section for, at the time of receiving an object portion designation from said object portion designation section and an image recording method designation from said image recording method designation section, reading from said storage section said menu items relating to said designated object portion and image recording method and forwarding said read-out menu items to said display section, for, at the time of receiving a routine menu item designation, reading said routine menu item or items from said storage section and forwarding the same to said display, and for, at the time of receiving a required menu item selection from said selection section, forwarding to said read-out means and/or said image processing means said read-out condition and/or said image processing condition corresponding to said required menu item.

2. A radiation image read-out apparatus according to claim 1 wherein said processing section is provided with a counter for counting the number of times each menu item is designated through said selection section and the routine menu items are changed to the ones most frequently designated.

3. A radiation image read-out apparatus comprising:

(i) read-out means for scanning with a light beam an image recording sheet on which a radiation image of an object has been stored, detecting light representing said radiation image emitted from said image recording sheet, and converting said detected light into an image signal, (ii) image processing means for receiving said image signal from said read-out means and carrying out image processing of said image signal, and (iii) menu item display and selection means for displaying at least some of a large number of menu items classified in accordance with image recording conditions used at the time said radiation image of the object was recorded such that each menu item corresponds to a specific read-out condition and/or image processing condition to be used at the time of obtaining said image signal, enabling selection of a single menu item from among said menu items, and forwarding to said read-out means and/or said image processing means a read-out condition and/or image processing condition corresponding to said selected menu item, as one of said image read-out conditions wherein said menu item display and selection means is constituted of:

(a) a storage section for storing said large number of menu items and said large number of read-out conditions and/or image processing conditions corresponding to said menu items, (b) an object portion designation section for designating, as one of said image recording conditions, the portion of said object whose image was recorded, (c) an image recording method designation section for designating, as one of said image recording conditions, said image recording method by which the image was recorded, (d) a mode selection section for selecting one menu from among a plurality of menus constituted by classifying a large number of menu items which have once been classified with respect to all possible combinations of object portion and image recording condition, (e) a display section for displaying image menu items, (f) a selection section for selecting the required one of said menu items displayed on said display section, and (g) a processing section for, at the time of receiving an object portion designation from said object portion designation section and an image recording method designation from said image recording method designation section, reading from said storage section those menu items relating to said designated object portion and image recording method which belong to said menu designated in advance in said mode selection section and forwarding said read-out menu items to said display section and for, at the time of receiving a required menu item selection from said selection section, forwarding to said read-out means and/or said image processing means said read-out condition and/or said image processing condition corresponding to said required menu item.

4. A radiation image read-out apparatus according to claim 3 wherein said processing section is provided with a counter for counting the number of times each menu item is designated through said selection section and the menu items belonging to the menu ordinarily designated in advance are changed to the ones most frequently designated.

* * * * *